(12) United States Patent
Chu

(10) Patent No.: US 8,712,556 B2
(45) Date of Patent: Apr. 29, 2014

(54) COMPOSITE CONDUCTIVE PADS/PLUGS FOR SURFACE-APPLIED NERVE-MUSCLE ELECTRICAL STIMULATION

(75) Inventor: Jennifer Chu, Haverford, PA (US)

(73) Assignee: JusJas LLC, Haverford, PA (US)

( * ) Notice: Subject to any disclaimer, the term of this patent is extended or adjusted under 35 U.S.C. 154(b) by 362 days.

(21) Appl. No.: 12/625,667

(22) Filed: Nov. 25, 2009

(65) Prior Publication Data

US 2010/0256722 A1   Oct. 7, 2010

Related U.S. Application Data

(60) Provisional application No. 61/165,753, filed on Apr. 1, 2009.

(51) Int. Cl.
*A61N 1/00* (2006.01)

(52) U.S. Cl.
USPC .......................................................... 607/145

(58) Field of Classification Search
USPC .......................................................... 607/145
See application file for complete search history.

(56) References Cited

U.S. PATENT DOCUMENTS

| | | | |
|---|---|---|---|
| 4,196,737 A | | 4/1980 | Bevilacqua |
| 4,736,752 A | | 4/1988 | Munck et al. |
| 5,203,330 A | * | 4/1993 | Schaefer et al. ............... 600/384 |
| 2003/0195587 A1 | | 10/2003 | Rigaux et al. |
| 2007/0142891 A1 | * | 6/2007 | Stanley ........................... 607/144 |
| 2008/0027508 A1 | * | 1/2008 | Chu ................................ 607/48 |

FOREIGN PATENT DOCUMENTS

JP   2008-284203   11/2008

OTHER PUBLICATIONS

International Search Report and Written Opinion of International Searching Authority mailed Aug. 27, 2010 in corresponding PCT Application No. PCT/US2010/020749.
U.S. Appl. No. 11/470,757 entitled, "Intramuscular Stimulation Therapy Using Surface-Applied Localized Electrical Stimulation", filed Sep. 6, 2006 (non-published).

* cited by examiner

*Primary Examiner* — Christopher D Koharski
*Assistant Examiner* — Nadia Ahmad
(74) *Attorney, Agent, or Firm* — Banner & Witcoff, Ltd.

(57) ABSTRACT

Composite electrode pads/plugs are configured to be utilized in an electrical stimulator device, particularly one designed to provide surface-applied electrical twitch obtaining intramuscular stimulation (eToims®). The composite pads/plugs include a porous liquid absorbent (e.g., felt) plug sized to be placed in a receptacle of the stimulator device, and a composite pad of porous liquid absorbent (e.g., cotton) material that covers the plug. In an embodiment, the composite pad is formed of cotton stuffing material encased between two sheets of cotton mesh/pad material. The composite pads/plugs can serve to increase, and improve wetting of, the surface area which contacts the patient and delivers the electrical stimulation. In addition to convenience of application, the disclosed structures have been found to help reduce sharp pain felt by the patient during stimulation, without interfering with the ability of the electricity to penetrate deeply in order to provide effective eToims®.

20 Claims, 9 Drawing Sheets

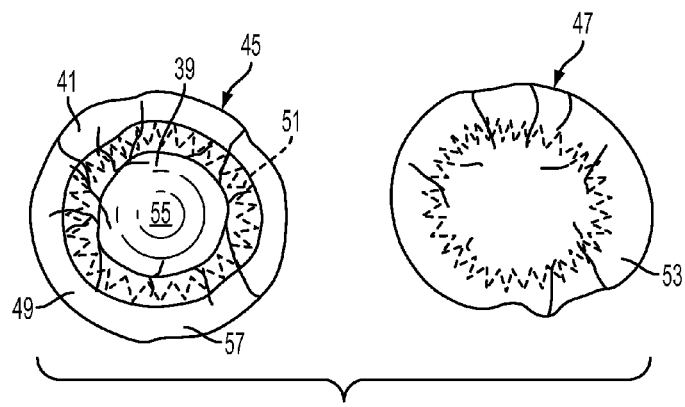
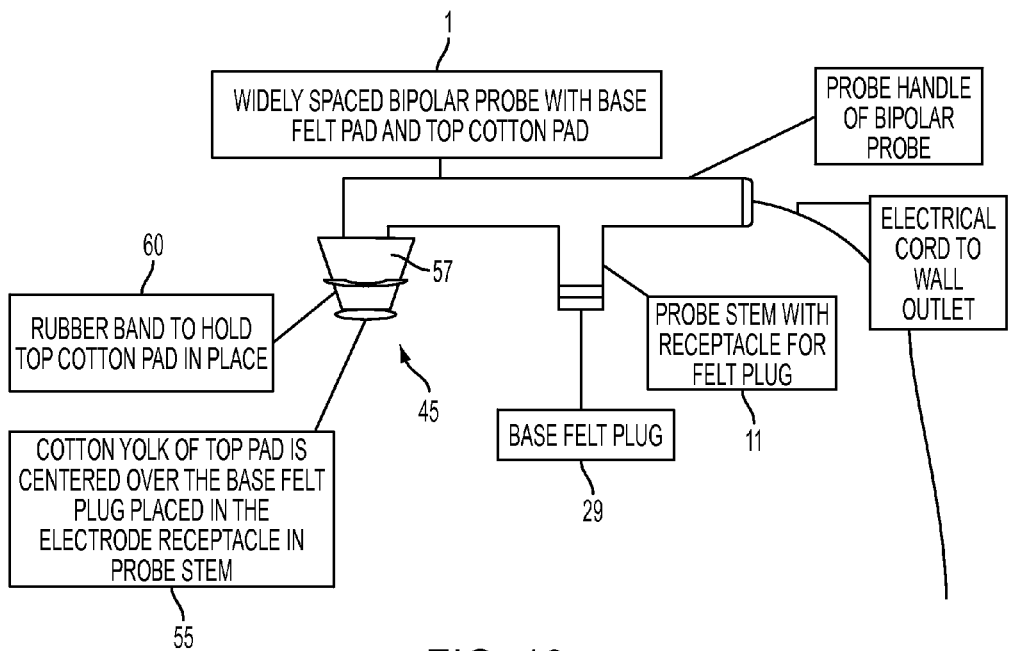
FIG. 9
FIG. 10

COMPOSITE CONDUCTIVE PADS/PLUGS FOR SURFACE-APPLIED NERVE-MUSCLE ELECTRICAL STIMULATION

This application claims the benefit of prior co-pending U.S. provisional application Ser. No. 61/165,753, filed Apr. 1, 2009, the disclosure of which is incorporated herein, both expressly and by reference, in its entirety.

FIELD OF THE INVENTION

The invention relates generally to an electrical stimulator device. More specifically, the invention provides composite conductive pads/plugs for a device used for nerve and muscle stimulation through surface application of electricity.

BACKGROUND OF THE INVENTION

Bipolar stimulator probes attachable to an electrical stimulator device or an electromyographic (EMG) device are commercially available for surface stimulation of peripheral nerves. Such apparatus provide both a stimulation electrode and a reference electrode on a single device. There are also bipolar bar electrode configurations, and sets of separate (individual) electrodes, for surface recording of nerve and muscle action potentials, and that can also serve to provide electrical muscle stimulation.

These types of devices can be used in surface stimulation for eliciting muscle twitches of the type sought in a muscle pain and discomfort relieving method developed by the present inventor, referred to as Surface Applied Electrical Twitch Obtaining Intramuscular Stimulation. This methodology is described in the present inventor's U.S. patent application Ser. No. 11/470,757, entitled "Intramuscular Stimulation Therapy Using Surface-Applied Localized Electrical Stimulation," filed Sep. 6, 2006, which is hereby incorporated by reference in its entirety. Treatments utilizing the methodology are clinically offered by the present inventor, and assignee Jus-Jas, LLC, under the service mark eToims®. For convenience, this service mark will be used herein to refer to this methodology as offered by the inventor and/or Jus-Jas, LLC or its affiliates. This technique involves the provision of brief electrical stimulation at multiple motor end-plate zones in many muscles. It is important that the stimulation method be "user friendly," to both patient and treating clinician. That is, the stimulation should not cause significant additional discomfort to the patient and the method should be easy to apply for the clinician.

Commercially available standard bipolar stimulating probes have an inter-probe distance of 2 cm or less between the active and reference electrodes. This type of bipolar stimulation induces significant stimulation pain making it undesirable for use in the eToims® procedure. In addition, due to the close proximity of the active and reference electrodes, twitches that may be elicited with such devices are small and have low forces, and therefore do not provide significant pain relieving effects. Similarly, as mentioned, surface electrodes that can be used for recording as well as stimulation purposes are available in the form of a bar electrode pair. Such devices have an inter-electrode distance of about 3-4 cm, and thus the problem of inducing stimulation pain arises if these devices are used to perform eToims®. Stimulation/recording electrodes are also available as separate (individual) electrodes. However, separate individual electrodes are less than ideal for use in the eToims® procedure, since both the active and reference electrodes have to be moved in bi-manual fashion to multiple stimulus and reference sites, thus slowing down and encumbering the eToims® procedure and making the procedure more difficult for the clinician.

The performance of eToims® using this inventor's bipolar probe with widely spaced electrodes (described in U.S. application Ser. No. 11/830,235, filed Jul. 30, 2007, published on Jan. 31, 2008, under No. 2008-0027508 A1, hereby incorporated by reference in its entirety) advantageously facilitates a methodology wherein: (1) the stimulation does not induce additional pain to a patient who is already in pain, or cause new pain to a client who has no pain but wants to obtain a relaxing massage effect to relieve muscle tightness/discomfort; and (2) the stimulation is beneficially able to penetrate the deeply situated motor endplate zones or neuromuscular junctions. In eToims®, it is desirable that the stimulation be carefully titrated between the patient's tolerance to pain and the clinician's need for using the stimulus strength and pulse width most appropriate to be able to penetrate through skin, subcutaneous tissue and the muscles, to stimulate deep motor endplate zones. In situations where the patient is unable to tolerate stimulation pain, the stimulus parameters often have to be reduced to make the treatment more comfortable for the patient. Often when the stimulus has to be reduced enough not to cause pain to the patient, only the superficial motor endplate zones can be stimulated. For those with discomfort/tightness or mild acute pain, this superficial muscle relaxation caused by the tissue mobilization effect of eToims® provides a scientific massage effect. This scientific massage effect can be sufficient to relieve discomfort or subclinical pain more significantly than that which can be obtained with manual massages. However, this precludes the deep tissue mobilization effects needed to produce neuromuscular pain relief for those patients with significant chronic pain.

A hallmark of eToims® is the ability to achieve elicitation of twitches that will move an associated joint in the direction of action of the stimulated muscle. These twitches have such a strong recoil effect on the hand holding onto the probe that the probe may be lifted or displaced off the surface of the stimulated muscle. The best pain relieving results with eToims® occurs with the elicitation of these large force twitches, qualitatively termed by the inventor as "movers". To achieve optimal pain relieving results during an eToims® session, it is important to quickly locate and stimulate the irritable motor endplate zones that elicit the most forceful twitches (movers) in as many muscles as needed to reduce the pain/discomfort symptoms.

If the muscle tissues are tight because of underlying pain or if the patient voluntarily or involuntarily tenses and contracts his/her muscles because of stimulation pain, electrical stimulation of the deep motor endplate zones is difficult since insufficient electricity will reach the deeper layers of the muscles. This is due to the electricity being filtered or buffered by the overlying tight muscle tissues. In such situations, the twitches elicited may not have sufficient force to move the joint in the direction of action of the treated muscle but still may have capacity to rock or shake the joint, qualitatively termed by the inventor as "shakers". These types of twitches that rock or shake the joint (shakers), will have a recoil effect on the clinician's hand holding onto the probe, though not as strong as those twitches that can move the joint. This recoil effect on the hand holding onto the probe differentiates twitch forces that shake the joint from those twitches which do not have joint play, i.e. no joint movements or shaking effect. The twitches that have ability to shake the joint also have pain relieving therapeutic effects but the pain relieving effects are sub-optimal compared to the twitches that move the joint in the direction of action of the stimulated muscle. The twitches that do not have any recoil effect on the hand holding onto the probe and thus have no joint play arise from stimulation of the superficial motor end-plate zones. These types of weak twitches are adequate to relieve muscle discomfort/tightness and/or even mild acute pain due to the stretching effects on the surface muscles in spasm. However, the weak twitches are not strong enough to stretch deep, tight and shortened muscles in strong spasm closest to the bone and joint to relieve deep neuromuscular pain/tightness as that which occurs in those who have chronic pain.

The mechanism which underlies pain relief related to the force of the twitches can be explained by the fact that damaged motor end plate zones or neuromuscular junctions trigger muscles to spasm and become tight producing pain through a vice-like effect on the pain sensitive intramuscular blood vessels and nerves as well as a strong traction effect on underlying pain sensitive bone and joints. Unlike other methods, eToims® targets pain and discomfort at these damaged points, releasing muscle tightness and spasm. eToims® stimulates deep motor endplate zones causing deep tight tissue within muscles to contract or twitch with surface applied electrical stimulation. These twitches are immediately accompanied by muscle relaxation which release tightness and increase intramuscular blood flow to restore circulation to damaged motor endplate zones allowing them to heal immediately in acute cases and over time with continued regular eToims® in chronic cases. With regular eToims® treatments, injured or tight muscles can properly heal, leading patients to enjoy an active daily life with continued improvement in range of body motion, accompanied by a decrease in pain and discomfort thus increasing their quality of life. In the process mentioned above, when muscle spasm is released, internal muscle stretching occurs. eToims® can be differentiated from other types of invasive and non-invasive neuromuscular stimulation by this ability to perform effective deep internal muscle stretching from stimulation of deep motor endplate zones (also known as neuromuscular junctions or trigger points).

For eToims® to be able to optimally achieve deep motor endplate zone stimulation without undue additional pain to the patient, the conducting properties of the electrode are important. If the electrode is rigid or inflexible and if it does not conform to uneven skin surfaces, there will be uneven dispersion of electricity and stimulation received by the deep motor end plate zones will be inconsistent leading to unpredictable pain relieving results. Also, the uneven electrical dispersion can cause stimulation pain to the patient. If the conduction property of the electrode is poor, stimulation of the deep motor endplates is often not achievable. On the other hand, even though deep stimulation is possible by increasing the stimulus strength and pulse width, if it is at the expense of introducing too much stimulation discomfort to the patient, patients will voluntarily and/or involuntarily tighten up the muscles defeating the purpose of deep stimulation. In fact the patient may even ask for cessation or termination of the stimulation session and not return for further eToims® sessions. Another alternative is to give prescription pain relieving medications half-hour to one hour before the stimulation so that the patient can tolerate the treatment. This is disfavored by this inventor, however, because it will then limit the treatment to only patients who are willing to take the medications to undergo the treatment. The potential treatment pain will also deter those healthy clients from trying eToims® as a scientific massage to relieve muscle tightness and discomfort. A goal of this inventor's implementation of eToims® is to encompass such generally healthy clientele and patients within the community of individuals undergoing regular treatment regimens over the long term, so that they can continue to enjoy an increase in, and prolongation of, quality of life.

eToims® results are best when applied prior to developing pain or as soon as possible after development of acute pain, preferably within 24 hours, since the muscles are not as tight and eToims® has potential to effectively relieve acute pain completely, even with one session or a few sessions, and thus prevent the development of chronic pain. Through experiencing pain relief with eToims®, and by reducing the stimulation discomfort during eToims®, patients and healthy clientele can be encouraged to return for further treatments on a regular basis for continuing benefits that the treatments can provide. Using effective and comfortable stimulation of deep motor endplate zones also has the potential to prevent healthy clientele, and those suffering from acute and chronic pain, from experiencing sudden pain onset, by keeping the muscles relaxed. This is due to the ability of eToims® to provide exercise and stretch effects to muscles which increases the blood supply to the neuromuscular junctions allowing them to heal rapidly on injury. eToims® can thus increase the safety margin that neuromuscular junctions have from compromise in situations of sudden or repetitive trauma that occurs with activities of daily living, sports, work, recreational activities, etc., in healthy people as well as those suffering from acute and chronic pain.

For electrical stimulation purposes, the common electrodes used for the nerve conduction velocity determination portion of electrodiagnosis are saline soaked small, disposable felt pads of about 7 mm in diameter and about 5 mm in height. FIG. 1 shows a bipolar probe 1 with widely spaced electrodes, constructed in accordance with the inventor's previously referenced U.S. application Ser. No. 11/830,235. The present inventor has used felt plugs 3, 5 of a diameter appropriate to fit receptacles 7, 9 for electrodes provided on the stems or arms 11, 13. Such a tool 1, equipped with felt plugs 3, 5 positioned in the cylindrical cup-like receptacles 7, 9 thereof, is shown in FIG. 1, in use applied against a patient's skin/flesh 14. FIG. 2 shows the tool grasped but out of contact with a patient. The same tool 1, with the felt plugs removed from the receptacles 7, 9, is shown in FIG. 3, thus revealing circular electrode plates 15 and 17 inset slightly at the ends of the tool stems 11, 13. It will be appreciated that one of the stems (stem 11) of the tool 1 is fixable in various positions along a slot 19 (visible in FIG. 3) extending along a tubular combination handle and cross-connection member 21, to provide different relatively wide spacings of the electrodes. Also visible in the figures, protruding laterally from opposite sides of the tubular cross-connection member 21, are finger operable wheels 23, 25 which control the pulse duration (ms) and stimulus strength (mamps). At the top, between the wheels, is a push-button 27 serving as a stimulation initiating trigger switch (best seen in FIGS. 2 and 4).

The felt plugs 3, 5 themselves (e.g., SAE felt specifications Grade #F-5 at 12.24 lbs per sq.yd, 1" to Grade #F-10 at 8.48 pounds per square yard, 1", F-10 preferable since it is softer and easier to soak through) are shown in FIG. 5. These felt plugs 3, 5, having a diameter of about 1" and a thickness of about ½", are pre-soaked, preferably overnight in plain water or 10% saline, to facilitate conduction. These felt plugs 3, 5 fit the probe receptacles 7, 9 snugly needing no adhesive taping to hold it in place. However during eToims®, the patient contact surfaces of the felt plugs 3, 5 dry easily making the stimulation sharp and painful for the patient. There is thus a need for frequent re-wetting of the patient contact surface of the felt plugs 3, 5 to reduce the pain during stimulation, which is time-consuming to the clinician during the eToims® procedure. Frequent wetting of the patient contact surface of the electrode with saline solution to aid the stimulation leaves dried salt all over the stimulation sites such that the dried salt has to be cleaned off from the patient's skin at the end of the procedure, adding more time to the procedure. Additionally, felt is abrasive and can produce allergic reactions or rash to those susceptible, and felt is best not used for direct contact against skin for surface electrical stimulation purposes especially where repetitive and repeated stimulation is needed. The felt plugs 3, 5 are also relatively inflexible and do not conform to the shape of uneven skin surfaces making the dispersal of electricity into the tissue uneven. This contributes to unnecessary pain during electrical stimulation.

BRIEF SUMMARY OF SELECTED INVENTIVE ASPECTS

With the foregoing in mind, the present inventor devised a new practical approach for equipping an electrical stimulation tool with electrode pads providing favorable characteristics both in terms of patient comfort and treatment efficacy. In particular, in accordance with an aspect of the invention, a composite electrode pad is provided for use in an electrical stimulator device. The composite pad includes a casing formed of porous liquid absorbing sheet material. A porous liquid absorbing stuffing, fill, or batting is contained within the casing so as to form, with the casing, a relatively thick porous liquid absorbing pad portion. A relatively thin drape portion extends outwardly from the pad portion.

In accordance with another aspect, the invention resides in a composite electrode pad/plug for an electrical stimulator device, including, in addition to the aforesaid composite pad structure, a plug of porous liquid absorbent material retained in contact with a side of the pad. In a preferred embodiment, the pad components (e.g., sheet and fill) are formed of cotton material, and the plug is formed of felt.

In accordance with a further aspect, the invention provides a bipolar stimulator probe assembly including an active stimulator electrode, a reference electrode and a user handle provided as part of a single tool. The probe tool comprises a spaced electrode mounting structure fixing the positions of the electrodes with respect to each other, and at least one of the electrodes comprises a composite electrode pad as aforesaid, wherein the relatively thin drape portion is connected to the electrode mounting structure to secure the composite electrode pad over an associated one of the electrodes. Preferably, a plug of porous liquid absorbent material (e.g., felt) is retained in contact with a side of the pad and an associated one of the electrodes, within a receptacle of the electrode mounting structure.

The above and other aspects, objects, features and advantages of the invention will be readily apparent and fully understood from the detailed description that follows, taken in conjunction with the appended drawings.

BRIEF DESCRIPTION OF THE DRAWINGS

FIG. 9 is a top plan view of a pair of composite conductive pads in accordance with an aspect of the invention.

FIG. 10 is a diagrammatic side elevation view of a bipolar stimulation probe with a composite pad/plug in one of the receptacles, in accordance with an aspect of the invention.

Figure 1:
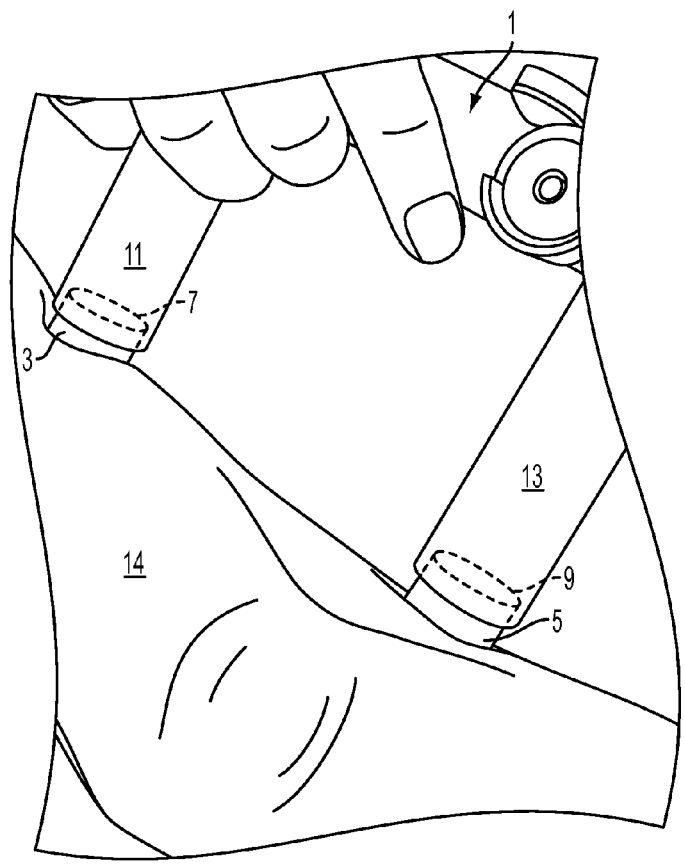
FIG. 1 is a perspective view of a related art bipolar stimulation probe equipped with felt electrode pads, being used on a patient.
Figure 2:
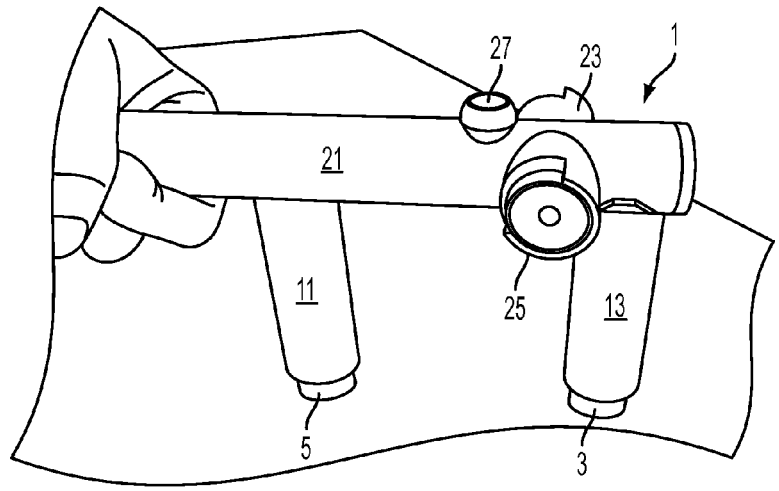
FIG. 2 is a further perspective view of the bipolar stimulation probe shown in FIG. 1.
Figure 3:
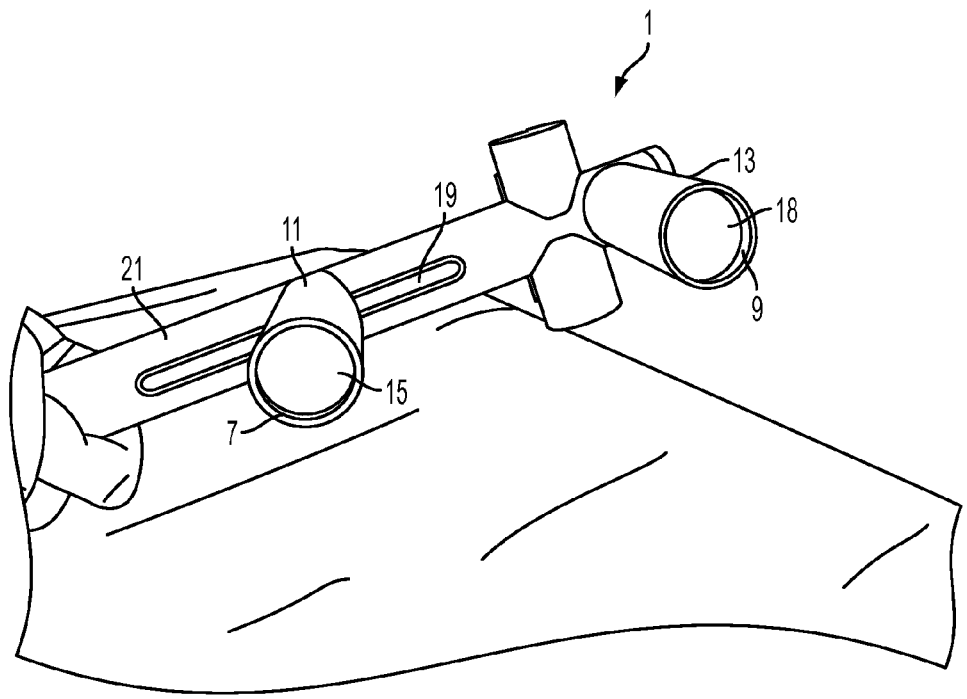
FIG. 3 is a perspective view of the underside of the bipolar stimulation probe, showing the receptacles that can be used for application of composite conductive pads/plugs in accordance with an aspect of the invention.
Figure 4:
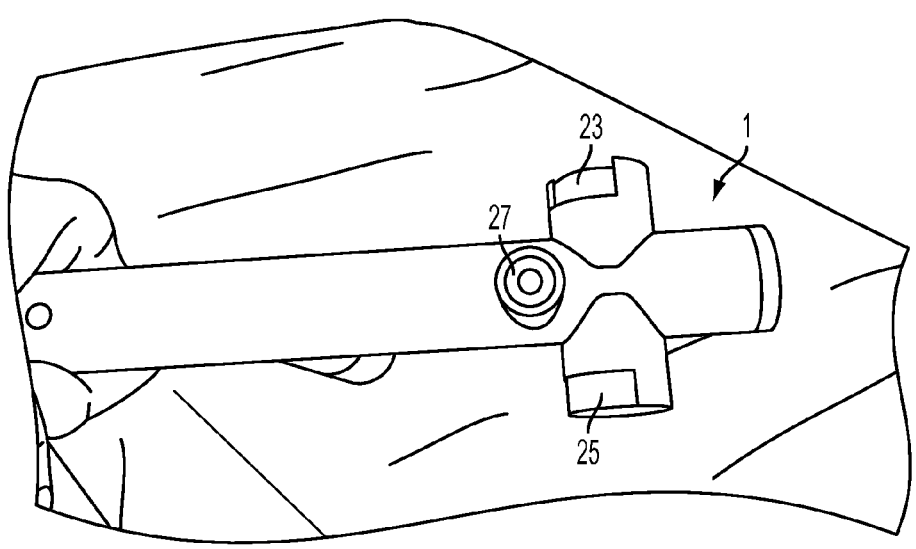
FIG. 4 is a top-side perspective view of the bipolar stimulation probe, with control members visible.
Figure 5:
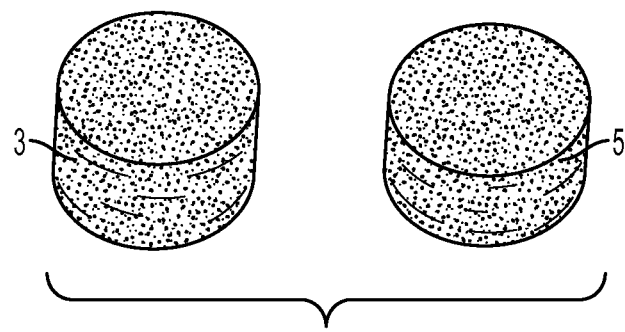
FIG. 5 is a perspective view of a pair of felt plugs of the type installed in the probe tool shown in FIGS. 1 and 2, having a thickness of about ½" inch (may also be used in composite conductive pads/plugs in accordance with an aspect of the invention).

DETAILED DESCRIPTION OF EXAMPLE EMBODIMENTS (AND THE INVENTOR'S DEVELOPMENT OF SAME)

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope of the present invention.

To address the above-described shortcomings associated with the use of felt plugs alone as porous liquid absorbent skin contact electrode pads, the inventor tried using, in conjunction with the inventor's bipolar probe tool (shown in FIGS. 1-4), 10% saline soaked large cotton balls weighing one gram placed in the electrode receptacle of the probe stem as conductive medium to reduce pain during stimulation. Cotton is soft, soothing, non-allergenic and also maintains the wetness longer. This reduces the number of times needed to re-wet the cotton ball during the eToims® procedures, compared to felt. However, the porous cotton ball did not provide enough stimulation penetration capacity to reach deeper tissues. This was noted especially on stimulating large muscles such as the latissimus dorsi or gluteus maximus. Also, even though the pain experienced during the stimulation seemed to be less than that of the felt plug, there was still a significant level of sharp sensation felt during the stimulation.

To reduce the sharp sensation during stimulation, the inventor tried cotton products with different densities such as cotton batting, cotton ribbon, compressed cotton, flannel and 97% cotton mixed with 3% spandex as conductive materials. A difficulty encountered was that these types of cotton pads did not fit in snugly into the electrode receptacle on the probe stems (unlike the felt plugs) and taping was needed to hold these cotton pads in place to prevent them from falling off or dislodging during tangential stimulation. The pain of the stimulation was also not diminished compared to the felt plug. Also, the depth of stimulus penetration was not as deep with cotton pads compared to felt plugs of the same diameter of 1" and thickness of ½".

To overcome the difficulty associated with holding the cotton pads to fit snugly in the electrode receptacle on the probe stem, the inventor used a smaller diameter (½") and ½" thick felt plug and totally wrapped it with a cotton mesh/pad of the type commonly used for removing facial make-up (e.g., as available from Kosmetech Corp, Brooklyn, N.Y.). This packaged pad also did not stay snugly in place within the electrode receptacle in the probe stem and still needed taping to prevent it from falling off or dislodging during stimulation. Also, there was more pain during stimulation when using a smaller diameter felt plug. This confirmed that the larger diameter of the conductive medium was important to reduce the amount of pain felt during the stimulation.

Figure 6:
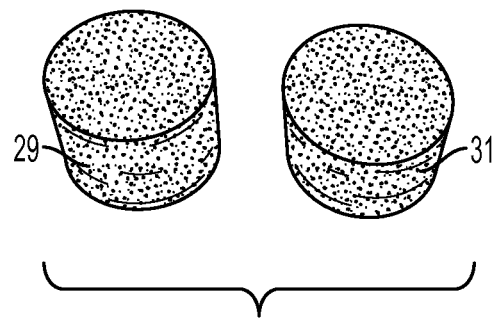
FIG. 6 is a perspective view of a pair of thicker felt plugs having a thickness of about ¾" inch, that may be used in composite conductive pads/plugs in accordance with an aspect of the invention.

To determine the significance of the thickness of the felt plug to the degree of stimulus penetration achieved, the inventor decided to use a thicker felt plug (29, 31) with a ¾" thickness and the same 1" in diameter (illustrated in FIG. 6). An assessment was made of the ability of this thicker felt plug (29, 31) to help facilitate stimulus penetration through large muscles such as the gluteus maximus and latissimus dorsi. The thicker felt plug (29, 31) wetted with 10% saline did deliver the necessary penetration essential to excite deep motor endplate zones. This was evidenced by the ability of the twitches to cause the stimulated gluteus maximus to move the hip joint into abduction in an antigravity manner with the patient in a sidelying position. Similarly, stimulation of the motor endplate zones of the latissimus dorsi muscle in the sidelying position was able to readily produce shoulder movements into adduction. This confirmed for the inventor that the thickness of the plug was important for being able to penetrate deep into the muscle, since such movements were not achieved with the felt plugs 3, 5 measuring ½ " in thickness with the same diameter of 1".

However, due to the sharp sensation still associated with using felt plugs, the inventor decided to use a one gram weight large cotton ball to cover the patient contact surface of the felt plug. The cotton ball was spread out to mushroom over the top and sides of the exposed felt plug which sat tight in the electrode receptacle in the probe stem. The overhanging cotton was then taped to the side of the probe stems using electrical tape.

This cotton ball, wetted with water or 10% saline, did reduce some of the sharp feelings associated with using just the wet felt plug alone for conduction. Additionally, it also reduced the number of times that re-wetting of the felt plug was required during the length of the eToims® procedure, since the cotton easily maintained its wetness and also automatically rewetted the surface of the felt plug against which it was opposed. The cotton-felt combination conductive medium was able to deliver electrical stimulation of the type required for optimal eToims®, i.e., stimulation that (1) does not induce undue additional pain to the patient who is already in pain or cause the stimulation of new pain to the client who has no pain but wants to obtain a relaxing massage effect to relieve muscle tightness/discomfort; and (2) is able to penetrate the deeply situated motor endplate zones or neuromuscular junctions. If the felt plug is not covered with cotton, the pain of the electrical stimulation leads to the patient tightening his muscles voluntarily and involuntarily. These tightened muscles prevent the electricity from penetrating to the deep motor endplate zones and also causes more pain since there will be more pain receptors per unit area in the tightened muscles. The use of a cotton ball over the felt plug allows the cotton to filter the electricity and takes out the sharp pain of the electrical stimulation. In this manner, the felt-cotton combination conductive medium allows electrical stimulation to the deep motor endplate zones since the electrical stimulation pain is reduced to the extent that the patient will not voluntarily or involuntarily tighten muscles which adds to the pain of the eToims® procedure. When the patient tighten the muscles voluntarily or involuntarily, more pain receptors are stimulated per unit area adding to the pain of the treatment and prevents the eToims® procedure from providing optimal results.

The inventor thus discovered that a cotton-felt combination provided a highly suitable and improved conductive medium for eToims® and nerve-muscle stimulation procedures. To be practical, the inventor recognized that the attachment of the cotton to the felt had to be made user-friendly. However, since the cotton and felt have different absorption capacities for fluid and since the felt plugs need to be presoaked preferably for one day or more, to make a prefixed cotton-felt combination plug was not ideal or practical. Gluing the cotton onto the felt presented the difficulty that the glue used, tended to lose its adhesiveness in the presence of wetness of the felt, and the cotton separated from the felt. Therefore, to blunt the sharp sensation felt by the patient during treatment, the inventor tried using two wet cotton balls placed on top of each other over the felt plug by taping them over the sides of the felt plug with electrical tape. This did not work well due to a "topheavy" situation where the unsupported cotton balls protruded too much beyond the edge of the felt plug, which itself protruded beyond the rims of the electrode receptacle encasing it.

Figure 7:
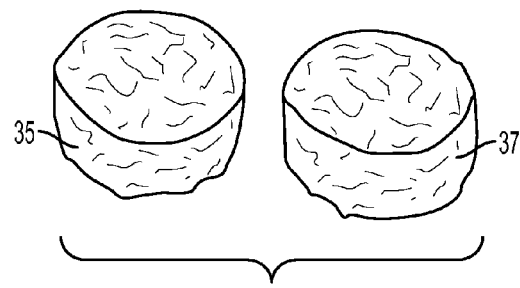
FIG. 7 is a perspective view of partially flattened cotton balls for use in composite conductive pads/plugs in accordance with an aspect of the invention.
Figure 8:
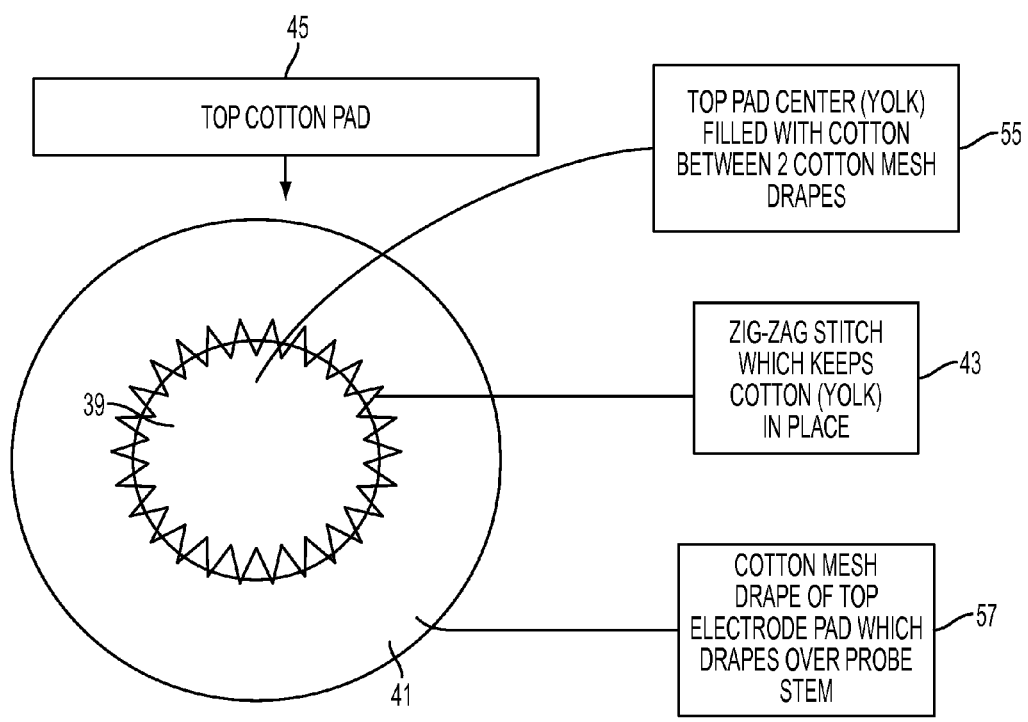
FIG. 8 is a diagrammatic top plan view of a composite conductive pad in accordance with an aspect of the invention.

The inventor thus came up with the idea of forming a composite top cotton pad by stuffing one or more spread out (i.e., partially flattened) cotton balls 35, 37 such as shown in FIG. 7, between two generic cotton meshes/pads 39, 41 of the type used for cleaning off facial makeup e.g., as available from Kosmetech Corp, Brooklyn, N.Y. In a particular embodiment, two cotton balls 35, 37 each weighing 1 gm in weight, are stuffed between two circular cotton mesh/pad pieces 39, 41. One mesh/pad 39 is 2¼" in diameter and the second mesh/pad 41 is 3" in diameter. (2¼" diameter textured cotton round pad 39, Kosmetech part # 99001, is made of 100% cotton and the 3" diameter plain large cotton round pad 41, Kosmetech part #99003, is also made of 100% cotton). The assemblage of two partially spread out and flattened cotton balls layered in the center of the 3" diameter round cotton mesh/pad 41 is then covered with the 2" diameter round cotton mesh/pad 39, and a zig-zag stitch 43 is made around the perimeter of the 2¼" diameter cotton mesh/pad 39. As seen in the diagrammatic view of FIG. 8, and the top plan view of two pads laid horizontal in FIG. 9, the cotton pads 45, 47 thus each generally resemble a sunny-side-up fried egg. In FIG. 9, the pad on the left 45 shows the cotton pad surface 49 with the exposed seam 51 between the two mesh/pad pieces, that is preferably used to contact the felt plug, and the one on the right 47 shows the opposite (smoother) cotton pad surface 53 that is preferably used to contact the patient. The stitching prevents the cotton center ("yolk") 55 from shifting during treatment. The height of the yolk part of this exemplary electrode pad is ¾". In this embodiment, there is at least approximately 0.5" of the 3" circular cotton mesh/pad excess around the yolk (the "egg-white" portion) 57, 59 to function as a drape 57 over the probe stem. The entire cotton pad 45 with two cotton ball "yolks" 55 in its dry state weighs 3.5 gms. The total cotton-felt combination conducting medium in its dry state is about 1.5" in height (0.75" height for the base felt plug 29, 31 (FIG. 6) and 0.75" height for the yolk part 55 of the top cotton pad). The diameter of the base felt plug is 1" and the diameter of the yolk portion 55 of the top cotton pad is 2".

Figure 11:
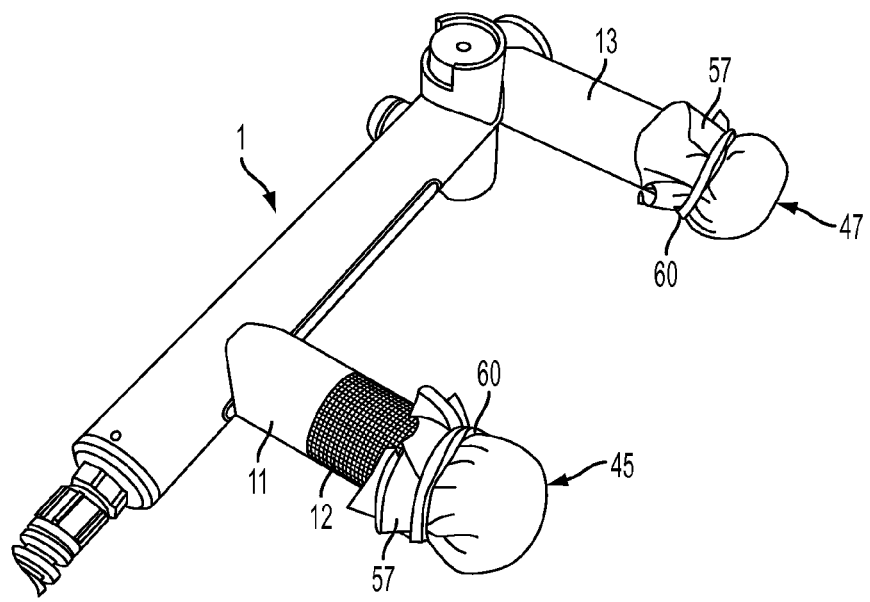
FIG. 11 is a side perspective view of a bipolar stimulation probe where composite pads/plugs are applied to both receptacles of the probe in accordance with an aspect of the invention.

The yolk portion 55 of the wetted cotton pad 45, 47 is then placed on top of the ¾" thick base felt plug 29, 31 (FIG. 6), which typically has been presoaked and snugly placed into the electrode receptacle in the probe stem. For use, the cotton pad 45, 47 is wetted, preferably and conveniently, the entire pad, although less than all could be wetted, e.g., just the yoke portion. The yolk portion 55 of the composite cotton pad is large enough to be able to cover the top and sides of the exposed felt plug protruding beyond the edges of the electrode receptacle in the probe stem 11, 13. The thinner drape portion 57 of the top cotton pad (the egg-white portion of the sunny-side-up egg) is then affixed to the probe stem 11, 13, preferably by an elastic (e.g., rubber) band 60 or other tie or fastener that may be easily and readily manually applied and removed (adhesive tape or the like could also be used). The resultant tool structure 1 is illustrated in FIG. 10 (composite cotton pad 45 applied to one of the two electrodes of tool 1) and FIG. 11 (cotton pads (45, 47) applied to both electrodes of tool 1). In FIG. 11, visible on stem 11 is a textured surface region 12 which may be provided on one or both of the stems and serve to assist with retention of the composite cotton pads on the stems (in overlying relationship with a base felt plug retained in an associated electrode receptacle).

In another version of the composite cotton pad, the drape portion 57 is 2" long so that the cotton pad can be secured in place even better over the probe stem with the rubber band, etc. The longer drape helps avoid dislodging of the cotton-felt combination conducting medium off the probe on encountering a forceful twitch, especially on stimulating at a tangent over uneven skin surfaces. The stimulus penetration of the cotton-felt combination conductive interface between stimulator probe and patient's skin for delivery of electrical stimulation is excellent for large muscles such as the gluteus maximus and latissimus dorsi.

In situations where deep stimulus penetration is not needed, as in the use with eToims® massages for those healthy clients who do not have pain complaints but have muscle discomfort and tightness symptoms, the cotton-felt combination conductive interface can be made with less center stuffing, e.g., center stuffing consisting only of one spread out large cotton ball weighing 1 gram. This top cotton pad with one cotton ball encased between a first cotton mesh/pad of 3" diameter and a second cotton mesh/pad of 2¼" diameter weighs 2.5 gms. This cotton-felt combination conductive interface in the dry state is about 1.25" in height (0.75" height for the base felt plug and 0.5" height for the yolk part of the top cotton pad). The diameter of the base felt plug is 1" and the diameter of the yolk portion of the top cotton pad is 2". The wetted pad's one-cotton ball yolk is placed over the wet felt plug inside the electrode receptacle in the probe stem and the sides of this cotton pad (the "egg-white" portion) are draped over the sides of the probe stem. The top cotton pad is then affixed to the probe stem, over the associated felt plug, with a rubber band, tie, etc.

In another embodiment that has given excellent results, a Jersey knit cotton (e.g., 6 oz material weight) is used in place of the cotton mesh/pad used for makeup removal, to encase one or more cotton balls (equivalent cotton stuffing, fill or batting could be used). Using the Jersey knit cotton wrap, use of only one cotton ball (instead of two) has sufficed for buffering the sharp pain associated with strong electrical stimulation needed for deep penetration. This is believed to be because the encased cotton ball is not intentionally flattened out but allowed to keep the original cotton ball round shape and there is stitching around the perimeter of the 2¼" wrap to prevent it from substantially flattening or spreading out. The reduction in the sharp pain encountered during strong electrical stimulation is enhanced due to the height of the round cotton ball which is greater than using two intentionally flattened out cotton balls in conjunction with the makeup removal cotton meshes/pads. It is believed that the relative thinness of the Jersey knit cotton wrap does not filter the electricity as much compared to that on using makeup removal meshes/pads, thus facilitating penetration to the deep motor endplate zones. The makeup removal meshes/pads are made of relatively hard compressed cotton whose absorbent quality and capacity to maintain the wetness are seemingly not as great as the thin Jersey knit cotton wrap, and which also filters the electricity to the extent that penetration to reach the deep motor endplate zones is reduced and made somewhat more difficult. As in the previous embodiment, the patient contact area may be a circular region of approximately 2" (5 cm) diameter, and the extra 1" (egg white portion) of the circular knit piece is used for draping over the probe stem.

Figure 12:
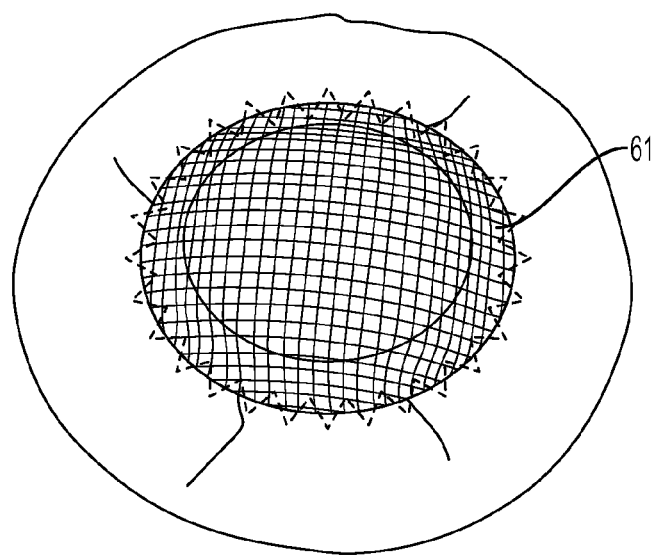
FIG. 12 is a top plan view of another composite pad in accordance with an aspect of the invention.
Figure 13B:
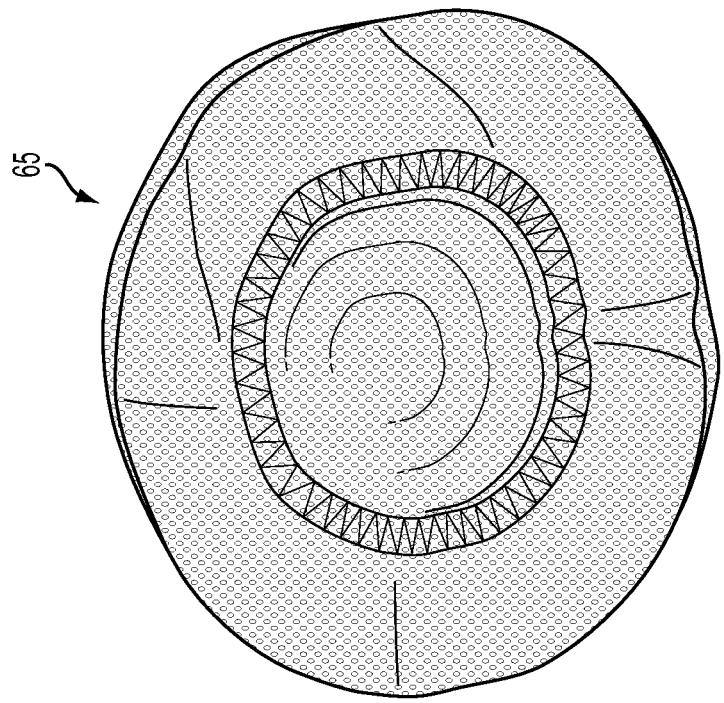
FIGS. 13*a* and 13*b* are top plan views of further embodiments of composite pads in accordance with aspects of the invention.
Figure 13A:
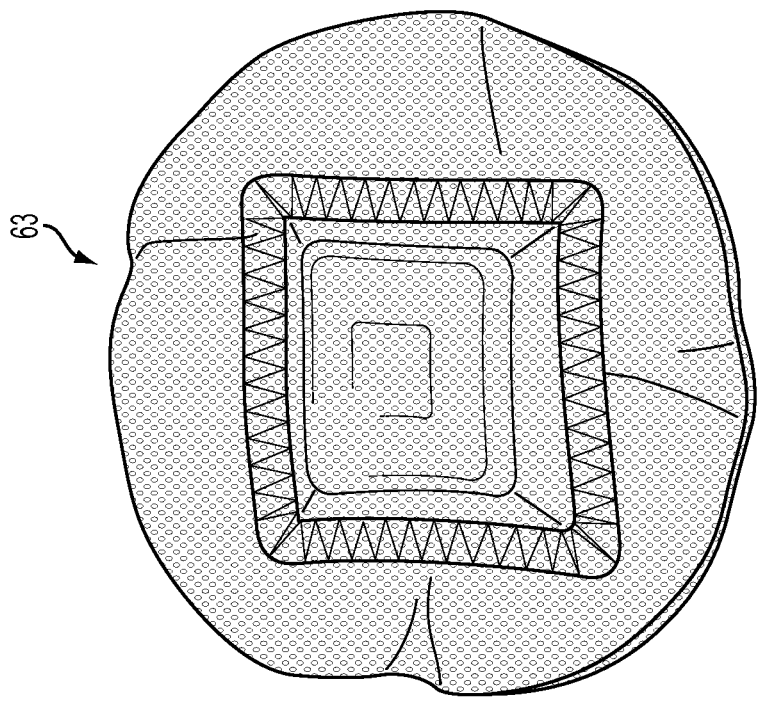

Yet, in another embodiment that has given even better deep motor endplate zones stimulation results than just using knit cotton on both sides to encase the cotton ball, the contact surface toward the felt plug has been replaced with soft, porous absorbent gauze 61 which is made of spun-laced non-woven cotton perhaps mixed with other synthetic fabric such as rayon or polyester as is available on the market, at about 30 gsm density/weight (FIG. 12). The improvement in muscle penetration results may be related to the ability of the porous spun-laced non-woven fabric to allow the passage of electricity more readily without filtering as much compared to the Jersey knit. The composite cotton pads, and the larger composite pads/plugs formed by the combination of the cotton pads with underlying felt plugs, are not only suitable for surface-applied eToims®, but can also be used in other situations where nerve and muscle stimulation is needed using surface application of electricity. This will include application to electrodiagnostic devices that require surface stimulation for nerve conduction studies, devices which provide transcutaneous electrical nerve stimulation (TENS) for pain relief and also powered muscle stimulators used in muscle pain relief and for improving range of motion.

The disclosed cotton composite conductive pads, and the underlying felt plugs, are typically, but not necessarily, disposed of as a set, after a single use (e.g., patient treatment session). In addition to their superior characteristics in the provision of electrical stimulation, and ease of application to and removal from the probe tool, the composite cotton pads also are hygienic, e.g., in that they protect the probe from coming in contact directly with the patient, and also protect the patient from potential bio-compatibility issues that may arise due to component materials of the probe or from the use of a felt plug alone.

What has thus been described is a new practical approach for increasing the surface area of the patient contacting conductive medium (electrodes) of an electrical stimulation tool, e.g., a bipolar stimulating probe with widely spaced electrodes designed for use in eToims® therapy. In accordance with an aspect of the invention, such an increase in surface area is accomplished using a top cushion cover of cotton rendered conductive by wetting or otherwise, fit over an underlying felt plug, to contact the patient. This obviates the need to increase the surface area of the electrode receptacle in the probe stems which would involve redesigning the probe at further expense to the manufacturer. Also, wider probe stems will make the probe tool heavier, potentially making it difficult and clumsy for the clinician to handle.

Increasing the surface area of the contact to the patient reduces the amount of current per square millimeter, and thus reduces the pain felt by the patient during stimulation. This reduces the potential for any skin burn which is also obviated by the fact that the top cotton cushion cover is preferably wet first with saline or water and the stimulation may only be for one second per stimulus site (usually only three twitches are elicited by stimulus site at 3 Hz, which dictates a one second time interval for the stimulation). The inventive composite conductive medium (wet base felt plug with top cotton cushion cover) also avoids use of exposed electrical wires or leads that have potential to burn the skin, and the use of electrolytic gels which may have allergic components causing biocompatibility issues. Felt has low impedance and helps with the conduction of the electricity, but sharp pain is felt by the patient. The cotton on top helps to avoid sharp pain but does not interfere with the ability of the electricity to penetrate deeply.

As one particular example, by using the cotton cushion cover with a 2" (5 cm) diameter circular contact area to the patient, the amount of current applied to the patient is 0.03 milliamp per square millimeter over one second of stimulation, if the clinician uses 3 Hz stimulation at 2000 µs pulse width with 100 milliamp current strength. In clinical situations, the pulse width used is usually no more than 500 µs, and therefore very little current passes to the irritable motor endplate zones. However, this very small current density applied over one second is sufficient to stimulate irritable motor endplate zones (that is how motor end plate zones may be defined).

For yet further aspects and embodiments of the invention, reference is made to FIGS. 13a-15. The composite conductive pads 63, 65 shown in FIGS. 13a and 13b respectively are made of spun-laced non-woven 100% cotton material from N.R. Spuntech Industries Ltd (Israel) for the two sheets, and a single 2 gm cotton ball for the fill. These materials have been tested in the laboratory and in have been found to be safe and biocompatible. The top and bottom sheets are of the same circumference with a diameter of 4 inches. The line of stitching may be circular around the cotton ball as shown in pad 65 of FIG. 13b, or may stitched around the cotton ball in a rectangular shape as shown in pad 63 of FIG. 13a.

Figure 14:
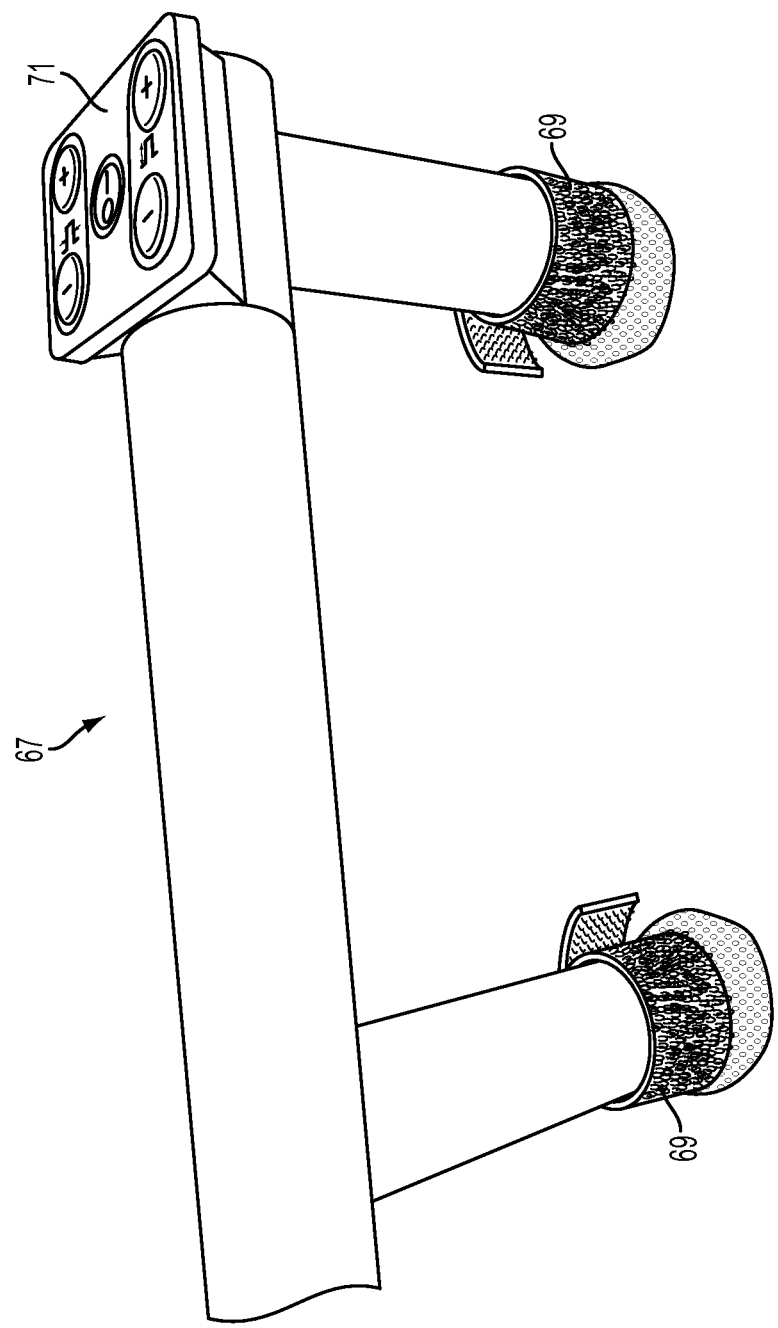
FIG. 14 is a side perspective view of a modified bipolar stimulation probe with composite pads/plugs applied to both receptacles of the probe in accordance with a further aspect of the invention.

FIG. 14 shows such composite cotton pads applied to the stem-end electrode receptacles of a modified probe tool 67. The patient contact area is approximately 2 inches in diameter. It has been found that with this embodiment of the composite cotton pads, one-half inch thick felt plugs may be used on the backsides of the cotton pads (within respective receptacles) without a decided difference in conduction properties compared to the three-quarter inch thick felt plug. Also, plain water may be used as the conduction liquid instead of saline. Plain water has been found to conduct well and has the benefit that the clinician does not need to clean off dried salt from the patient's skin after the eToims® procedure.

As further seen in FIG. 14, an elastic band or strap 69 (e.g., of 1" width) with Velcro-type hook and loop fasteners at the ends may be used, in place of closed loop rubber bands, to maintain the cotton pads on the probe stems (in overlying relationship with associated felt plugs fitted within respective electrode receptacles).

Figure 15:
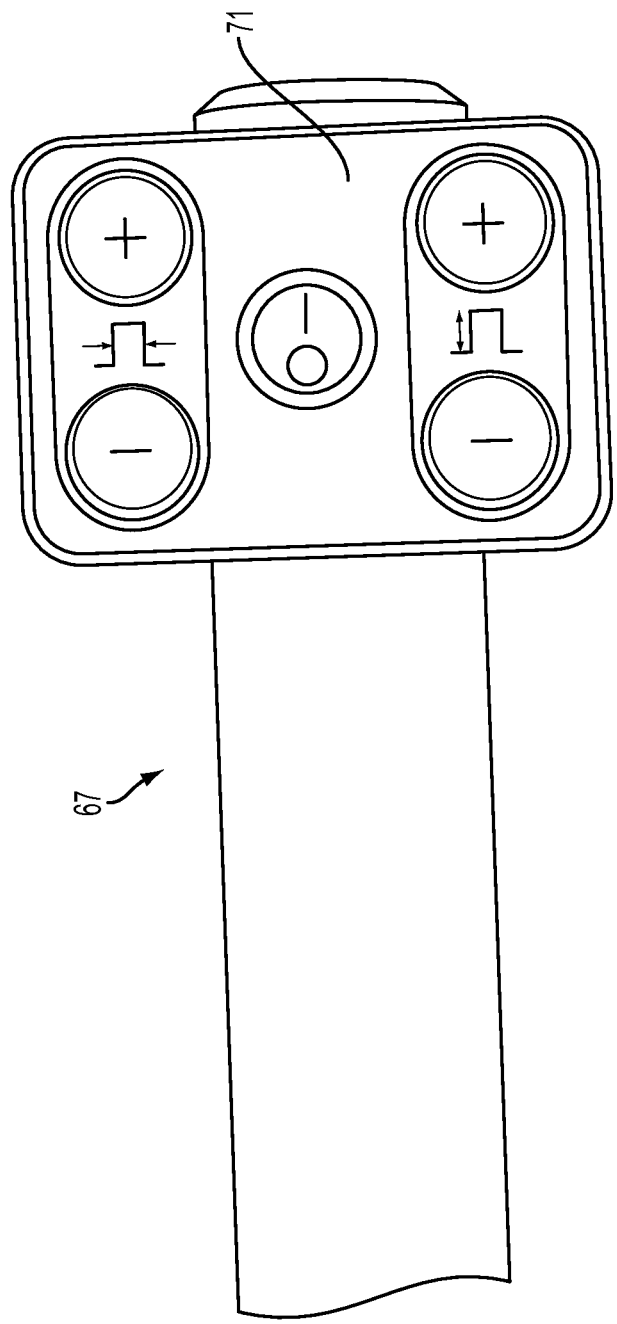
FIG. 15 is a top plan view of a control portion of the probe tool shown in FIG. 14.

Referring now to FIG. 15, it is seen that in the modified version of the tool 67 shown in FIGS. 14 and 15, the stimulation controls are provided on a touch pad 71, which may, e.g., comprise a set of membrane switches presenting soft, slightly elevated press-actuated pads or buttons. The top left (+) button may be pressed to incrementally increase the pulse width (microseconds—µs) of the electrical stimulation provided by the tool, and the bottom left (−) button may be pressed to decrease/decrement the pulse width (microseconds—µs) of the electrical stimulation. The top right (+) button may be pressed for incrementally increasing the stimulus strength (milliamps-mA) and the bottom right (−) button may be pressed for decreasing/decrementing the stimulus strength (milliamps—mA). The single push-button in the middle may function to start, stop and/or pause the stimulation.

It will be understood that while the invention has been described in conjunction with various embodiments and details thereof, the foregoing description and examples are intended to illustrate, but not limit the scope of the invention. Numerous other variations and arrangements are within the scope of the invention. This may include e.g., constructing the cotton pad from one, rather than two or more discrete cotton components, so long as comparable electrical and structural characteristics are achieved, and also potentially substituting another material or materials for the cotton, which may yield comparable results (such as cotton with polyester or rayon components or other non-allergenic materials which buffers the electrical stimulation without filtering it too much to the extent that it reduces the eToims results). Also, instead of a base felt plug, a tight cotton roll of the type used in dentistry, custom-made to fit snugly in the electrode receptacle in the probe stem may be used. The advantage of using a base cotton plug instead of a base felt plug is the ease in wetting the base cotton plug immediately and together with the top cotton pad. This makes it more user-friendly since the base felt plug may take a day for soaking through thoroughly). Variations may also include securing the cotton pad to the felt plug with a glue or adhesive that transmits electricity between the cotton pad and felt plug and which also does not lose its adhesiveness when wetted with water or saline; or stitching the cotton pad onto the felt plug; or other means of attaching the cotton pad to the felt plug to make a combination cotton-felt conductive medium to facilitate surface-applied electrical stimulation. It must also be noted that the diameters and the thickness of the cotton-felt composite pads and parts thereof (e.g., composite cotton pad sub-assemblies) can be changed and are not limited to the particulars of the illustrative embodiments described herein.

The invention claimed is:

1. A composite electrode pad for use in an electrical stimulator device, comprising:
   a casing formed of porous liquid absorbing sheet material;
   a porous liquid absorbing stuffing, fill, or batting contained within the casing so as to form, with said casing, a relatively thick porous liquid absorbing pad portion; and
   a relatively thin drape portion extending outwardly from said pad portion;
   wherein said drape portion extends outwardly from said pad portion about an entire outer periphery of said pad portion.

2. A composite electrode pad/plug for an electrical stimulator device, comprising the composite electrode pad according to claim 1; and a plug of porous liquid absorbent material retained in contact with a side of said pad.

3. The composite electrode pad/plug according to claim 2, wherein said plug comprises felt.

4. The composite electrode pad/plug according to claim 3, wherein said plug is cylindrical in shape and sized and positioned with respect to said first sheet such that it is, about its entire periphery, spaced inwardly from an outer perimeter of said first sheet, whereby said drape portion extends outwardly beyond said plug about the entire periphery of said plug.

5. The composite electrode pad according to claim 1, said electrode pad being formed by a first sheet of porous liquid absorbing material; and a second sheet of porous liquid absorbing material attached to said first sheet of porous liquid absorbing material so as to form said casing.

6. The composite electrode pad according to claim 1, wherein said fill, stuffing or batting comprises cotton material.

7. The composite electrode pad according to claim 6, wherein said fill, stuffing or batting comprises at least one cotton ball.

8. The composite electrode pad according to claim 5, wherein said first and second sheets of porous liquid absorbing material are attached to each other by a line of attachment extending about an outer perimeter of the pad portion.

9. The composite electrode pad according to claim 8, wherein said line of attachment comprises a line of stitching.

10. The composite electrode pad according to claim 1, wherein both said porous liquid absorbing sheet material and said porous liquid absorbing stuffing, fill, or batting comprises a cotton material.

11. A composite electrode pad/plug for an electrical stimulator device, comprising the composite electrode pad according to claim 10; and a plug of porous liquid absorbent felt material retained in contact with a side of said pad.

12. The composite electrode pad according to claim 10, wherein said porous liquid absorbing sheet material comprises a cotton mesh.

13. The composite electrode pad according to claim 10, wherein said porous liquid absorbing sheet material comprises a layer of Jersey knit cotton.

14. The composite electrode pad according to claim 10, wherein porous liquid absorbing sheet material comprises a spun-laced non-woven cotton.

15. A composite electrode pad/plug for an electrical stimulator device, comprising:
   a plug of porous liquid absorbent material; and
   a pad consisting essentially of cotton material in contact with and substantially overlying said plug.

16. A bipolar stimulator probe assembly including an active stimulator electrode, a reference electrode and a user handle provided as part of a single tool, wherein the probe tool comprises a spaced electrode mounting structure fixing the positions of the electrodes with respect to each other, and wherein at least one of said electrodes comprises a composite electrode pad, said pad comprising:
   a casing formed of porous liquid absorbing sheet material;
   a porous liquid absorbing stuffing, fill, or batting contained within the casing so as to form, with said casing, a relatively thick porous liquid absorbing pad portion;
   a relatively thin drape portion extending outwardly from said pad portion and being connected to said electrode mounting structure to secure said composite electrode pad over an associated one of said electrodes; and
   a plug of porous liquid absorbent material retained in contact with a side of said pad and an associated one of said electrodes, within a receptacle of said electrode mounting structure, wherein said plug is cylindrical in shape and sized to fit snugly within said receptacle, and wherein said drape portion extends outwardly beyond said plug about the entire periphery of said plug and is held in wrapping contact about the periphery of an associated arm portion of said electrode mounting structure.

17. The bipolar stimulator probe assembly according to claim 16, wherein both said porous liquid absorbing sheet material and said porous liquid absorbing stuffing, fill, or batting comprises a cotton material, and said plug comprises felt.

18. The bipolar stimulator probe assembly according to claim 16, wherein said drape portion is affixed to said associated arm portion by an elastic band.

19. The device according to claim 16, wherein top and side portions of the plug protrude from said receptacle, and said composite electrode pad completely covers the protruding top and side portions of the plug.

20. A composite electrode pad for use in an electrical stimulator device, comprising:
   a casing formed of porous liquid absorbing sheet material;
   a porous liquid absorbing stuffing, filling, or batting contained within the casing so as to form, with said casing, a relatively thick porous liquid absorbing pad portion; and
   a relatively thin drape portion extending outwardly from said paid portion:
   wherein said relatively thin drape portion extending outwardly from said pad portion is a continuous and integral extension of a piece of material comprising the porous liquid absorbing sheet material forming the casing.

* * * * *